United States Patent [19]
Phillips et al.

[11] 4,080,535
[45] Mar. 21, 1978

[54] GENERATOR CONDITION MONITOR FOR PARTICULATE DETECTION

[75] Inventors: David C. Phillips, Penn Hills Township, Allegheny County; William M. Hickam, Churchill Borough; Scott L. Anderson, Plum Borough, all of Pa.

[73] Assignee: Westinghouse Electric Corporation, Pittsburgh, Pa.

[21] Appl. No.: 715,258

[22] Filed: Aug. 17, 1976

[51] Int. Cl.² ............................................. G01T 1/18
[52] U.S. Cl. ................................. 250/381; 73/339 R; 250/382; 250/384
[58] Field of Search ....................... 250/381, 382, 384; 73/339 R

[56] References Cited
U.S. PATENT DOCUMENTS

| 2,968,730 | 1/1961 | Morris et al. | 250/384 X |
| 3,449,659 | 6/1969 | Boiziau | 250/381 X |
| 3,573,460 | 9/1966 | Skala | 250/381 |
| 3,714,421 | 1/1973 | Josias et al. | 250/381 |

Primary Examiner—Archie R. Borchelt
Attorney, Agent, or Firm—R. K. Robinson

[57] ABSTRACT

In a hydrogen cooled dynamoelectric machine, an ion chamber detector monitors thermally produced particulates. Specificity and sensitivity of the ion chamber detector are improved by applying an electrical potential of a limited predetermined range to the electrodes of the detector and operation of the detector occurs within a well defined subsaturation range.

10 Claims, 11 Drawing Figures

GENERATOR CONDITION MONITOR FOR PARTICULATE DETECTION

BACKGROUND OF THE INVENTION

1. Field of the Invention

This invention relates to improved apparatus for detecting an overheating condition in a gas-cooled dynamoelectric machine, and more particularly to an improved ion chamber apparatus for detecting the presence of submicron particles associated with overheating of parts in a gas-cooled turbine generator.

2. Description of the Prior Art

Large turbine generators are cooled by forcing a stream of a cooling fluid such as hydrogen over the heat producing parts of the machine. Because of the high flux densities present in the core of such a machine, localized overheating may cause degradation of the insulation disposed on the laminations and end turns. Because of the potentially catastrophic consequences of such degradation, it is desirable to provide an early warning of an overheating condition.

Apparatus such as the generator condition monitor has been developed to provide early warning of an overheating condition. The generator condition monitor is a highly sensitive device which rapidly detects the presence of particles in the hydrogen atmosphere of a turbine generator. Operation of the generator condition monitor is based on the principle that very high concentrations of submicron particles are produced whenever any material within the generator is heated sufficiently to initiate thermal decomposition. When an overheating situation arises within the generator, organic materials in the overheated area are affected first and degrade, producing particulates which enter the gas stream. In conventional practice, special organic compounds are deposited throughout the generator which particulate at much lower temperatures than most organic materials utilized in usual generator construction.

In one well known generator condition monitor, submicron particles are detected by their influence on the output current of an ion chamber which is arranged to collect the hydrogen ions which are produced by a low level radiation source in the hydrogen gas stream which carries the particles. In the absence of the particles, almost all of the hydrogen ions are collected, resulting in maximum output current of a magnitude determined by the strength of the radiation source and the ionization properties of the gas stream. With particles present, some ions combine with them. Because the particles are much larger than the ions, the mobility of the resultant charged particle is less, and relatively few are collected in the ion chamber. The result is a decrease in the output current of the ion chamber, this decrease being a function of the particle concentration and particle size. Such an arrangement is disclosed by Skala in U.S. Pat. No. 3,573,460. U.S. Pat. No. 3,427,880 issued to Grobel et al describes an application of such an ion chamber for detecting pyrolysis products resulting from overheating of generator insulation.

Although the apparatus described in the above-named patents have functioned adequately for the detection of overheating in certain generators, there have been occasions when more specificity and sensitivity would have been advantageous in determining the existence of a potentially damaging overheating condition. With improved specificity and sensitivity, an earlier warning of incipient failure within a generator can be achieved, which in turn would lead to an earlier shutdown of the machine and consequently less damage to existing insulation.

SUMMARY OF THE INVENTION

It has been determined and experimentally verified that the specificity (size of particle detected) and sensitivity of the conventional ion chamber detector is improved by operating the electrodes at an electric potential of a magnitude sufficient to establish a voltage gradient between the electrodes substantially within the range of 1.66 volts per centimeter to 6.66 volts per centimeter. During operation within this collector voltage range, a small change in the number of particles to be detected will cause a significant change in the output current. Therefore particles which have a high mobility (smaller size) will cause more of a change in the output current when compared with operation in a normal mode without the presence of pyrolysis products. The significance of operating the collector electrodes within a narrow voltage gradient range is based upon the following observations: (1) operation at relatively higher voltage gradients as taught by the prior art causes saturation; (2) sufficient numbers of ions for monitoring purposes are collected at relatively lower voltage gradients corresponding with operation below the saturation level; (3) smaller particles entrained in the gas stream have greater mobility than the larger particles; (4) the axial distance traveled by a particle through the collector is inversely proportional to the voltage gradient across the collector electrodes; and, (5) assuming laminar flow of the gas stream through the collector, and assuming a collector flow path of fixed length, the distribution of the particles within the collector chamber is such that only the smaller particles with higher mobility are collected during the limited transit time through the collector. Thus, the specificity and sensitivity of such a device is improved by carefully controlling the voltage applied across the collector plates within a voltage gradient range which is substantially less than the voltage gradient employed in similar prior art devices.

The foregoing and other objects, advantages and features of the invention will hereinafter appear, and for purposes of illustration, but not of limitation, an exemplary embodiment of the subject invention is shown in the appended drawing.

BRIEF DESCRIPTION OF THE DRAWING

The various

DESCRIPTION OF THE PREFERRED EMBODIMENT

Figure 1:
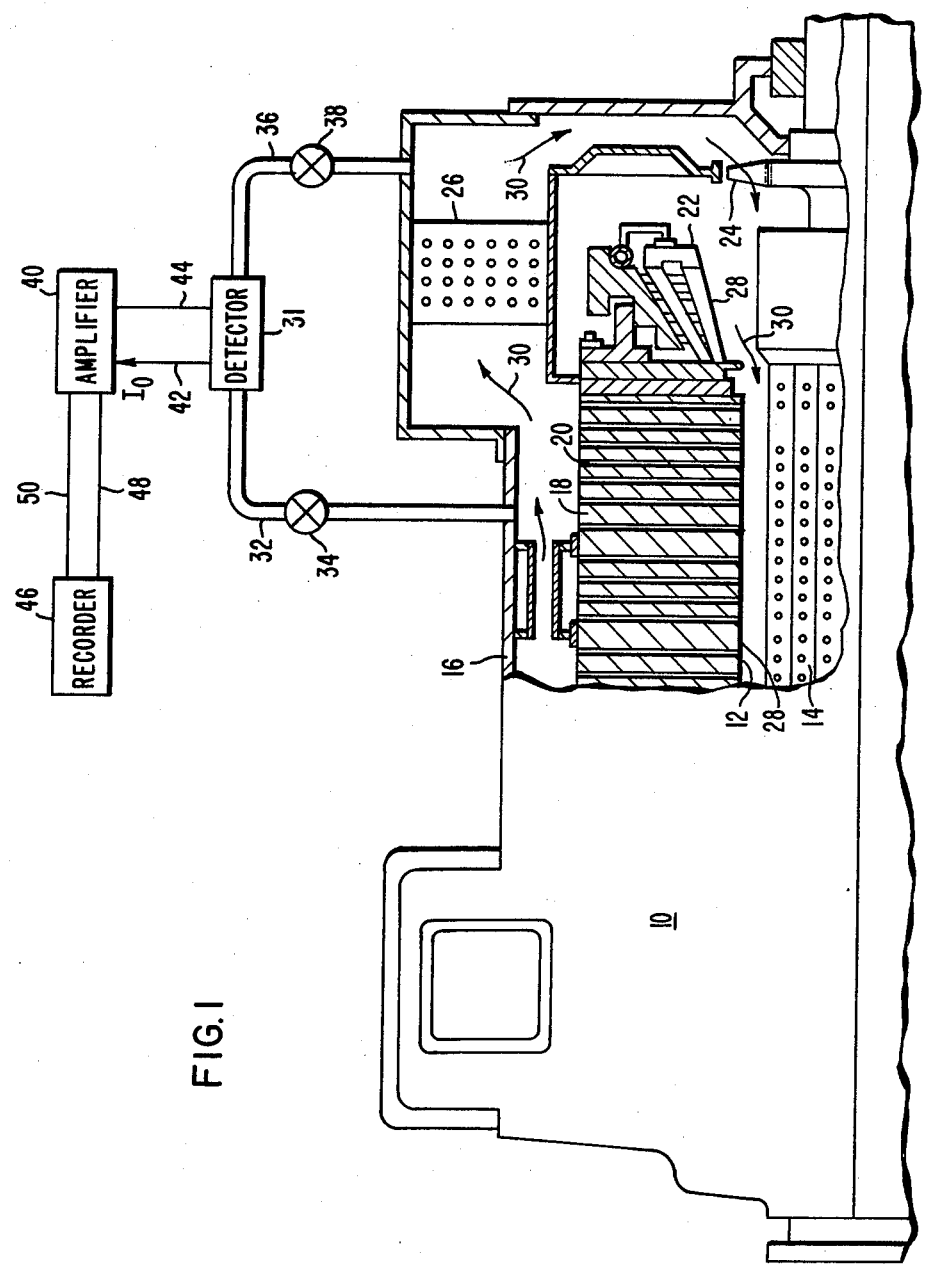
FIG. 1 is a simplified schematic view of a gas-cooled turbine generator, partly in cross-section, illustrating the overall arrangement.

The invention is shown in FIG. 1 in combination with a large gas-cooled turbine generator 10 which is typical of the type of dynamoelectric machine with which the present invention can be used to detect overheating. The generator 10 includes a stator member 12 and a rotor member 14 which are supported in the usual manner within a gas-tight housing 16. The stator core is comprised of magnetic laminations 18 which are separated by cooling ducts 20. The laminations are formed with slots within which a stator winding is disposed with end turn portions 22 extending at either end of the stator core. Means such as a rotor mounted fan 24 circulates a gas coolant, such as hydrogen, around the dynamoelectric machine and through the cooling ducts 20. Heat from the cooling gas is transferred away from the dynamoelectric machine 10 by means of a heat exchanger 26.

According to conventional practice, various portions of the stator core laminations 18 and end windings 22 are coated with organic materials such as epoxy and polymeric resins. These organic materials, when heated, emit submicron particles as pyrolysis products which are both detectable and identifiable. While the coatings referred to may be insulation material which is usually associated with the machine, special "sacrificial" coatings 28 may be applied to the various machine elements to produce thermal decomposition products before any of the normally present organic materials are affected. The circulating coolant gas entrains these decomposition products and carries them through the system as illustrated by the arrows 30.

Figure 2:
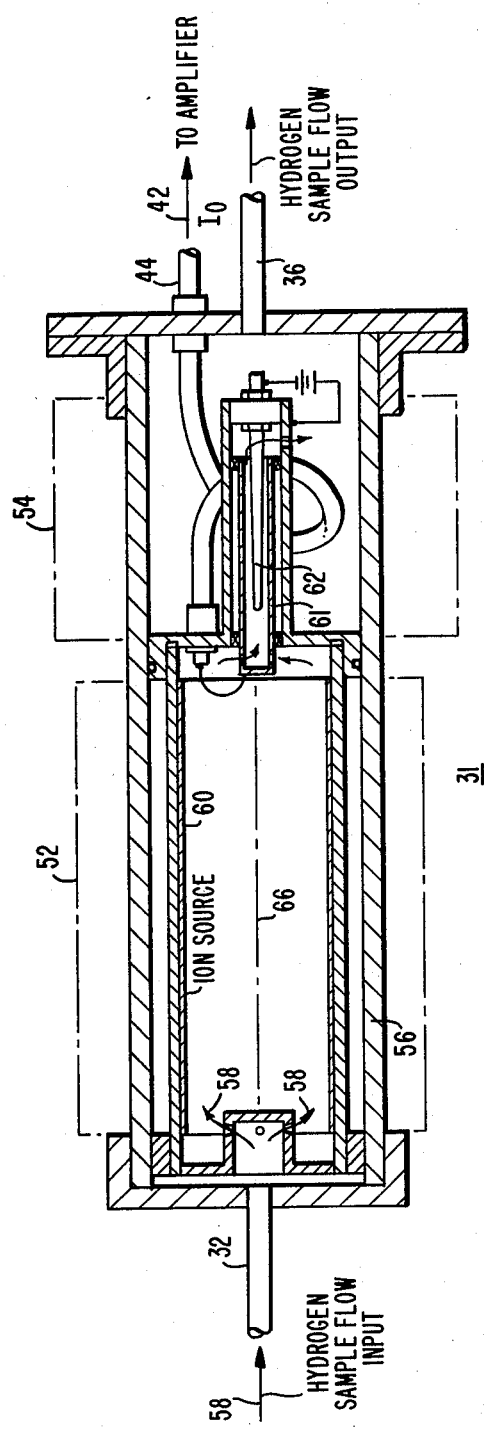
FIG. 2 is a schematic view of the ion chamber particle detector of FIG. 1.

A typical generator condition monitor which is suitable for detecting the presence of decomposition products in the dynamoelectric machine 10 comprises an ion chamber detector 31 as shown in FIGS. 1 and 2 of the drawing, and as described in the above-mentioned U.S. Pat. No. 3,573,460. A portion of "flow" of the cooling fluid is withdrawn from the high pressure side of the machine housing by a conduit 32 having a shutdown valve 34 connected in series fluid relation therewith. After passing through the detector, the fluid is directed back into the low pressure side of the dynamoelectric machine 10 by means of a return conduit 36 which also includes a shutdown valve 38. The detector 31 is electrically connected to an amplifier 40 by means of output conductors 42 and 44. The amplifier 40 may be of any suitable linear type and its output is connected to a recorder 46 by means of conductors 48 and 50.

Referring now to FIG. 2, the detector 31 comprises an ionizing section 52 and an ion collecting chamber 54 contained in a pressure housing 56. The coolant flow as represented by the arrows 58 passes through the ionizing section 52 in which a low level radiation source 60 is disposed. A convenient means for ionizing the hydrogen gas which has been used to good advantage in this detector comprises minute amounts of Thorium 232, which produces 3.99 Mev alphas, and has a half life of $1.32 \times 10^{10}$ years.

Hydrogen ions produced by the Thorium source 60 are carried by the coolant flow to the ion collecting chamber 54 which includes a pair of collector electrodes 61 and 62. Because of their high electrical mobility, most of the ions produced from the radiation source 60 are attracted to one of the collector electrodes, depending on the relative polarity of the ions and of the collectors, producing a current $I_o$. In the present example, the hydrogen ions are positively charged and are attracted to the electrode 62 which has been negatively charged by a bias potential E, thereby producing the current $I_o$ as they are collected. However, when overheating within the dynamoelectric machine occurs, decomposition products are present in the coolant, and some of the hydrogen ions become physically associated with them, thereby creating particle-ion combinations with a substantially reduced charge-to-mass ratio. Since the electrical mobility of the particle-ion combination is relatively low, only a few of the combinations are attracted to the collector electrode 62, resulting in a significant decrease in the collector current $I_o$. The current $I_o$ is transmitted to the amplifier 40 through the conductor 42 where it is amplified and recorded for continuous observation by means of the recorder 46; or, when the current $I_o$ falls below a predetermined level, an alarm (not shown) may be activated to provide an audible warning of generator overheating.

Theory of Operation

Figure 3A:
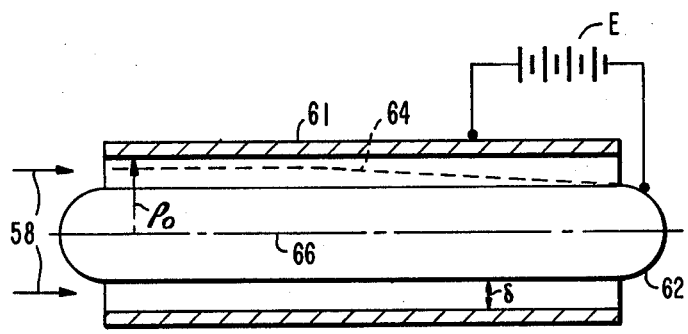
FIGS. 3A, 3B, and 3C show the geometry of the cylindrical collector electrodes of the ion chamber particle detector of FIG. 2 and also illustrate the precipitation of particles carried by laminar flow in an electric field.
Figure 3B:
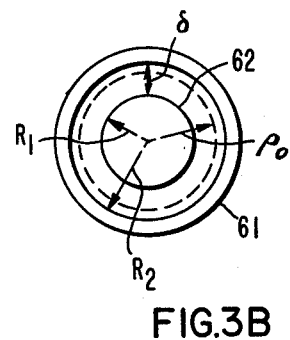
Figure 3C:
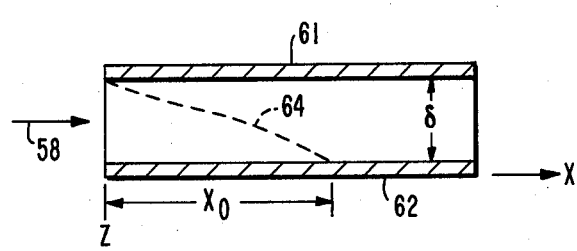

Referring now to FIGS. 3A, 3B, and 3C, consider the precipitation of charged particles from a laminar gas flow through a parallel-electrode condenser, for example, the electrodes 61, 62. Motion of particles in a direction (z) perpendicular to the plane of the electrode 62 is given by the equation $$v_z = EqB/\delta$$

where E is the voltage across the condenser electrodes, $\delta$ is the separation distance, $q$ is the charge on the particle, and B is the mechanical mobility of the particles. A hypothetical path of a particle is illustrated by the dashed line 64 in FIG. 3A and FIG. 3C. The electrical mobility ($\overline{u}$) is related to the mechanical mobility (B) by the formula $\overline{u} = qB/300$ and for simplification $\overline{u} = 300\ \overline{u}$.

If the potential difference is expressed in volts, the formula becomes $$v_z = (dz/dt) = Eu/\delta$$

Motion of the particle parallel to the condenser electrodes is expressed by the equation $$(dx/dt) = U(z)$$

where $U$ is the gas velocity.

From these equations it follows that a particle entering the condenser close to the electrode bearing a charge of the same sign as its own charge will reach the other electrode after traveling a distance $x_o$ (FIG. 3C) where $$x_o = \frac{\delta}{Eu} \int_0^\delta U(z)dz = \frac{U\delta^2}{Eu}$$

The distribution of mobilities, like the size distribution, is a continuous function which can, however, have several maxima. The number of particles with mobilities lying within the limits $u$ and $u + du$ is $$dN = f(u)du$$

where $f(u)$ is the distribution of mobilities of the particles. The longitudinal distribution of mobilities obtained as above reflects the distribution of mobility, the number of particles in the strip bounded by the coordinates $x$ and $x + dx$ being given by
$$dN = \phi(x)dx$$
where $\phi(x)$ is the longitudinal distribution of particles.

Consider the mobility of the particles through the cylindrical condenser (FIG. 3A). The current $I_o$ flowing to the electrode 62 is measured as a function of the potential (E) across the condenser, and the mobility distribution, $f(u)$. With laminar flow through such a condenser, the gas velocity, and hence also the velocity of the particles in a direction parallel to the axis 66 of the condenser, $V_x(\rho)$, is a function of the distance $\rho$ from the axis. The field strength H in a cylindrical condenser is equal to $$H = E/(\rho \ln [R_2/R_1]),$$

where $R_2$ is the radius of the outer electrode and $R_1$ the radius of the inner.

The radial velocity of the particles is therefore $$v = Eu/(\rho \ln [R_2/R_1])$$

Suppose the outside electrode 60 is positively charged. A positively charged particle travels towards the inner electrode 62, in time $dt$ a distance $$d\rho = - Eudt/(\rho \ln [R_2/R_1])$$

In the same time it moves along the axis of the condenser through $$dx = U(\rho)dt.$$

Elimination of $dt$ from these equations leads to $$dx = - U(\rho)\rho \ln\left(\frac{R_2}{R_1}\right)\frac{d\rho}{Eu}.$$

If the particle enters the condenser at a distance $\rho_1$ from the axis, it reaches the inner electrode 62 after traveling along it to a point $$x = - \frac{\ln(\frac{R_2}{R_1})}{Eu} \int_{\rho_1}^{R_1} U(\rho)\rho d\rho = \frac{\ln(\frac{R_2}{R_1})}{Eu} \int_{R_1}^{\rho_1} U(\rho)\rho d\rho.$$

If all the particles have the same mobility $u$ and the length of the condenser is L, the inner electrode 62 will be reached at some point in time corresponding to the condition $x < L$. Such particles have $\rho_1 < \rho_0$, where $\rho_0$ is the limit of integration in $$\frac{\ln(\frac{R_2}{R_1})}{Eu} \int_{R_1}^{\rho_0} U(\rho)\rho d\rho = L.$$

Thus, for a given potential E on the condenser, particles must enter it at a distance from the axis less than $\rho_0$ in order to be precipitated. Hence, the specificity (size of particle precipitated) and sensitivity of such a device can be markedly altered by varying the voltage gradient across the plates.

Experimental Verification

Figure 4:
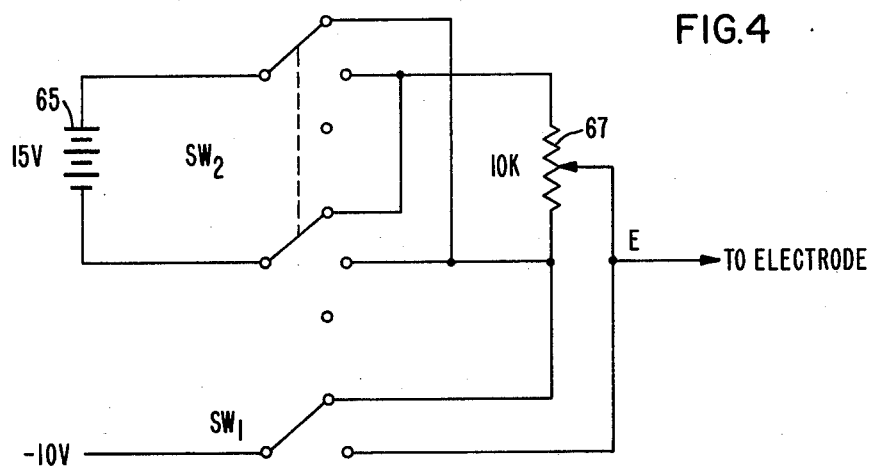
FIG. 4 is an electrical schematic diagram which illustrates a circuit which provides a variable voltage across the ion chamber collector electrodes of FIG. 2.

A circuit was designed to vary the voltage supplied to the center electrode 62 of the ion chamber. An electrode spacing distance $\delta = 0.30$ centimeters ($R_1 = 0.315$ cm; $R_2 = 0.615$ cm) was used throughout the experiment. A suitable circuit is shown in FIG. 4. It consists of a single pole double-throw switch (SW1) which provides a by-pass of the variable voltage system that allows the ion chamber detector 31 to be used in its normal mode of operation. A double pole three-position switch (SW2) connected across a 15 volt battery supply 65 allows the polarity of the battery input to the circuit to be changed and thus produces an addition or subtraction to the normally supplied −10 volts of the instrument. A variable 10K ohm resistor 67 determines the relative amount of change in the positive or negative voltage applied to the electrodes of the ion chamber. A voltage that continuously changes (i.e., a sweep voltage) could not be used because of severe "spiking" in the instrument ion current output that required several seconds to normalize after a small voltage change.

Figure 5:
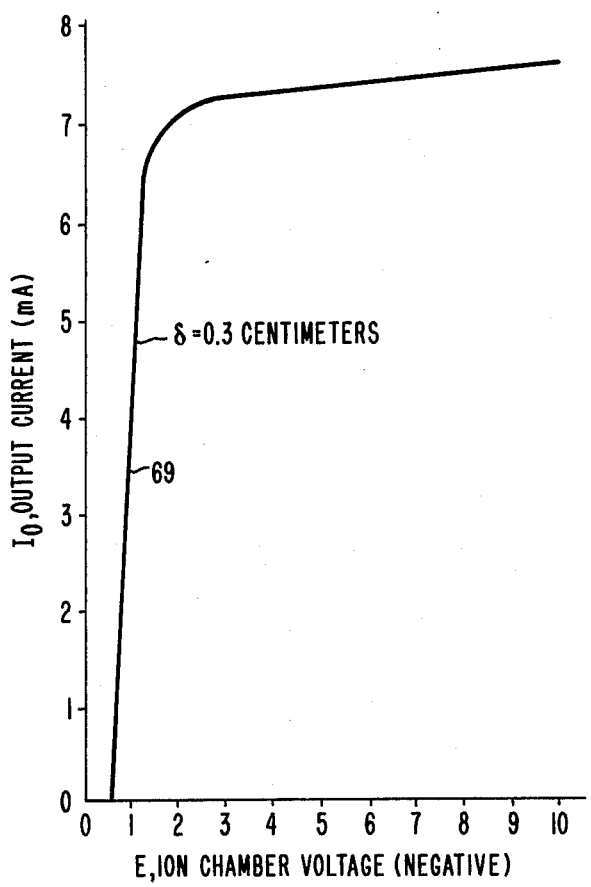
FIG. 5 is a graphical representation of the variation of the current output of the collector electrodes of the ion chamber particle detector of FIG. 2 as a function of ion chamber collector voltage.

The entire circuit was placed in series between the instrument supplied-voltage (−10 volts) and the ion chamber central electrode 62. Normal instrument operating conditions were employed (i.e., constant flow, pressure, and temperature). Applied voltage was varied between 0–10 volts in increments of approximately 1 volt with output ion current being read after a stabilization period of approximately one minute. The resulting curve 69 is shown in FIG. 5. At approximately $> -2$ volts saturation occurs and the output current curve flattens dramatically with each additional voltage increment having little influence on the output current. Hence, output current appears most sensitive in the subsaturation range 0.5–2.0 volts, which corresponds to a voltage gradient of 1.66–6.66 volts per centimeter for a typical electrode spacing $\delta$ of 0.30 centimeters. In this subsaturation region, a small change in the number of particles to be detected will cause a significant change in output current. This in turn means that particles having a high mobility (smaller size) will cause more of a change in output current when compared with the contribution of ions associated with normal mode of operation. Hence, specificity and sensitivity of the instrument is enhanced by operation in the subsaturation region rather than operation in saturation as taught by the prior art.

The precipitation of aerosol particles in the presence of an electric field at saturation and subsaturation levels is explained in more detail in standard texts such as N. A. Fuchs, *The Mechanics of Aerosols,* Pergammon Press (MacMillan Co.) 1964, and T. A. Rich et al, "On the Time Required for Aerosols to Reach Equilibrium", Geof. pura e appl., Vol. 51, 1962, pp. 217-24.

Figure 6:
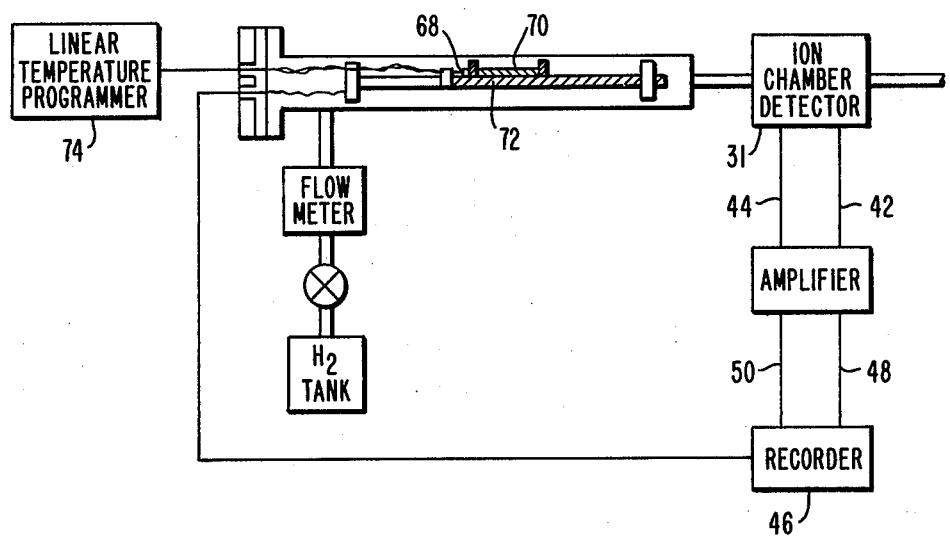
FIG. 6 is a schematic diagram of a system utilized for generating particulates.

The apparatus shown in FIG. 6 was used to generate particulates to show the response of the improved instrument to various particulate matter. A detailed description of the function and operation of the apparatus shown in FIG. 6 is given in a copending application by D. C. Phillips and J. D. B. Smith entitled "Malonic Acid Derivative Composition for Forming Thermparticulating Coating," Ser. No. 706,089, filed July 16, 1976. Accurate temperature measurements were made through a Chromel-Alumel thermocouple 68 attached to a stainless steel boat 70 which rests directly on a strip heater 72. The entire assembly was mounted on insulating stand-off pedestals within a stainless steel tube (1 inch o.d.). A phase controlled temperature regulator and programmer 74, connected through a sealed endplate to the boat 70, acted as a temperature control on the heater. The output of the thermocouple 68 and detector 31 were monitored on a two-pen potentiostatic recorder 46. Hydrogen, at a constant flow rate of 6 liters/minute, was passed over the samples contained in the boat 70. A 6° C/minute heating rate was maintained in each experiment. The temperatures were read from the recorder 46: the threshold temperature which corresponded to the onset of thermoparticulation (as shown by an initial fall-off in amplified ion current) and the alarm temperature which signified a 50% decrease in the ion current (usually 0.8–0.4 mA).

Figure 7:
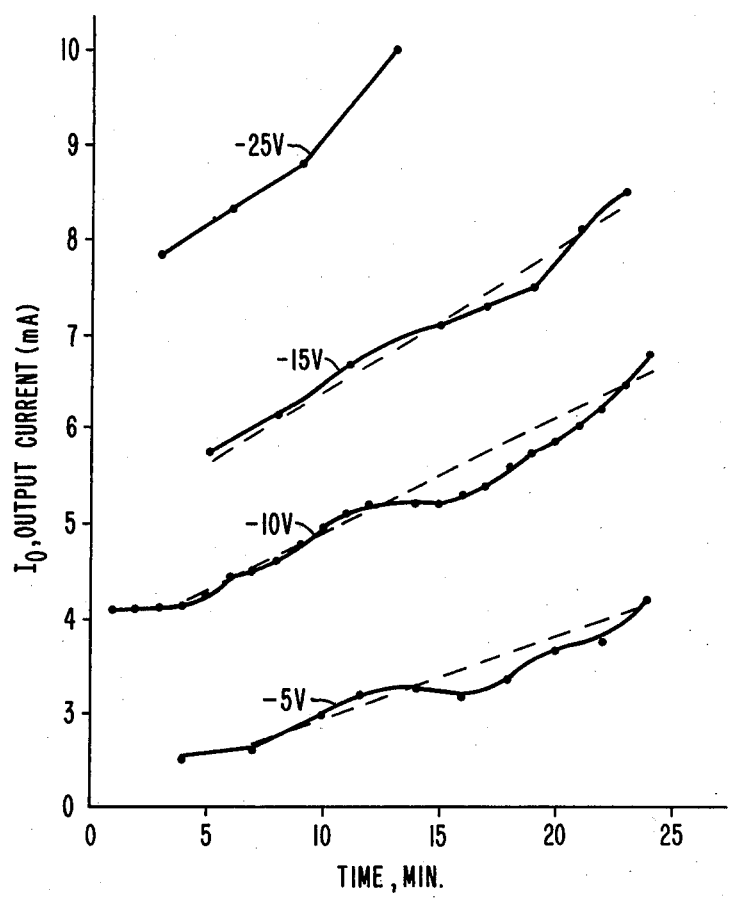
FIG. 7 is a graphical illustration of output current $I_o$ at various voltages during particulation as a function of time.

With the apparatus of FIG. 6 providing a source of particulates, the voltage supplied to the ion chamber was varied using the circuit of FIG. 4. The "normal" base level was established with −10 volts. The voltage was varied from −25 to −5 volts; output currents were read at each voltage level. the results are shown in FIG. 7. Since the number of particulates does not change rapidly with time, the decrease in output current (increase in particulation signal strength) with a decrease in the magnitude of negative voltage is due to a greater number of particles with higher mobility not being detected. This demonstrates that the instrument has a higher sensitivity when the "normal" −10 volts applied to the electrode is decreased.

A number of straight-chain fatty acid series $C_nH_{2n}O_2$ were thermoparticulated in the apparatus of FIG. 6; the individual members comprised of $C_9H_{18}O_2$, $C_{10}H_{20}O_2$, $C_{11}H_{22}O_2$, and $C_{12}H_{24}O_2$; each adjacent member differs in atomic size by 2-3 Angstroms. In one instance, the prior art −10 volts potential difference was employed; in the second instance, a reduced voltage of −0.9 volts was utilized. This enabled a comparison of the sensitivity of the detector 31 in both modes to be made as illustrated in FIGS. 8 and 9.

Figure 8:
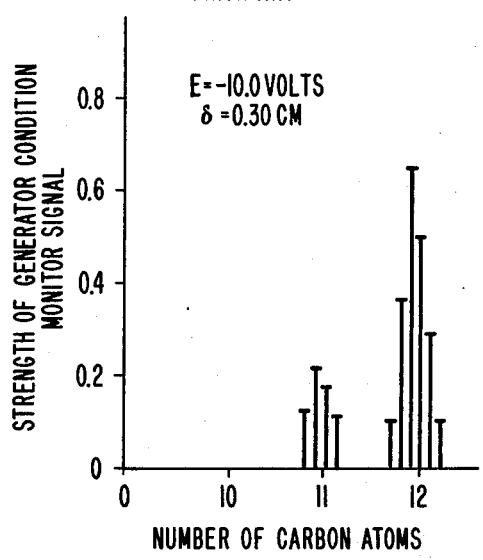
FIG. 8 is a graphical representation of the strength of a signal which is a function of the number of ions collected by the ion chamber particle detector which is electrically biased according to the teachings of the prior art; and, FIG. 9 is a graphical representation similar to that of FIG. 8 which illustrates the improvement in specificity and sensitivity for an ion chamber particle detector which is electrically biased according to the teachings of the present invention.
Figure 9:
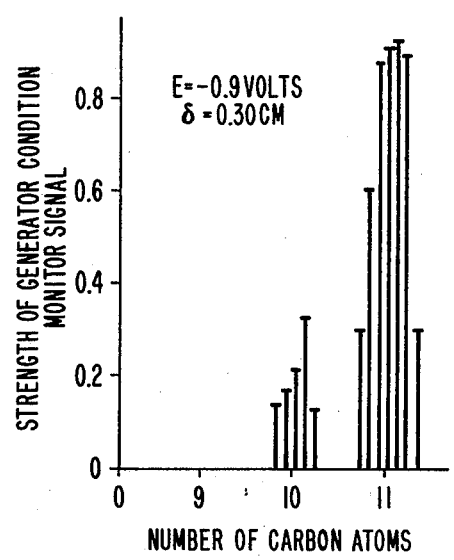

The temperatures of thermoparticulation for each series is shown in Table 1, whereas the strength (or lack of strength) of detector 31 signal is shown in FIG. 8 and FIG. 9. When signals were not observed, the heat supplied to the system was terminated at 275° C. In the conventional −10 V mode of operation of the ion chamber, the limit of detection is the $C_{11}$ compound. However, in the −0.9 V operation of the ion chamber, the smaller $C_{10}$ compound can be detected and thus becomes the limit of the −0.9 V series. Hence, a greater instrument sensitivity (or specificity) was found in the improved (−0.9 V) case.

A commercially available polymer (polymethyl methacrylate) was thermoparticulated in several experiments; each experiment utilized a different potential difference across the ion chamber. The potential difference range was −25.0 to +2.0 volts. The results are shown in the first section of Table 2. Voltages between zero and −1.0 were found to be the most sensitive for detection of particulate species from overheated polymethyl methacrylate. "Alarm" temperatures varied from 276°–290° C.

This showed that voltages between zero and −1.0 were optimum for detection; however, current drift at the very low voltages caused an insensitive signal response, so that the upper end of the range was chosen.

From Table 2, it can be seen that alarm temperatures were lower than the improved ion chamber arrangement was utilized; temperature spread was ∼15°–30° C. Hence, it is apparent that an earlier warning of incipient failure would be indicated when using the improved ion chamber instrument. Further, since the generator could be shut down sooner, less thermal damage would occur to the existing insulation.

TABLE 1

Comparison of Fatty Acid Thermoparticulation Signals Using "normal" and "improved" Ion Chambers

| Sample | Ion Chamber Voltage (V) | Instrument Gain | Initial Current (mA) | Thermoparticulation Temperature (° C) 1st | Alarm | Sample Weight* (mg) |
|---|---|---|---|---|---|---|
| Lauric Acid ($C_{12}H_{24}O_2$) | −10.0 | 79 | 0.5 | 155 | 161 | 9.5 |
| Undecanoic Acid ($C_{11}H_{22}O_2$) | −10.0 | 79 | 8.7 | 160 | 168 | 15.8 |
|  | −0.9 | 84 | 8.0 | 162 | 165 | 23.5 |
| Decanoic Acid ($C_{10}H_{20}O_2$) | −10.0 | 79 | 8.5 | no alarm** |  | 15.1 |
|  | −0.9 | 84 | 8.0 | 160 | 200 | 28.1 |
| Nonanoic Acid ($C_9H_{18}O_2$) | −0.9 | 84 | 8.0 | no alarm** |  | 18.5 |

*Weight of sample remaining in boat after run was zero (i.e., all the compound had thermoparticulated).
**No alarm to temperature of 275° C.

TABLE 2

Comparison of Thermal Alarm Temperatures Utilizing "normal" and "improved" Ion Chamber Instruments

| Sample | Ion Chamber Voltage (V) | Instrument Gain | Initial Current (mA) | Thermoparticulation Temperature (° C) 1st | Alarm |
|---|---|---|---|---|---|
| Polymethyl- | −25.0 | 80 | 0.81 | 278 | 290 |

TABLE 2-continued

Comparison of Thermal Alarm Temperatures Utilizing "normal" and "improved" Ion Chamber Instruments

| Sample | Ion Chamber Voltage (V) | Instrument Gain | Initial Current (mA) | Thermoparticulation Temperature (° C) | |
|---|---|---|---|---|---|
| | | | | 1st | Alarm |
| methacrylate | −10.0 | 80 | 0.80 | 278 | 281 |
| | −5.0 | 80 | 0.80 | 275 | 278 |
| | −2.0 | 80 | 0.785 | 273 | 279 |
| | −1.0 | 84 | 0.825 | 271 | 276 |
| | −0.7 | 92 | 0.85 | 271 | 277 |
| | 0.0 | 76 | 0.10 | 270 | "278"[a] |
| | +1.0 | 69 | 0.10 | 275 | "280"[a] |
| | +2.0 | 69 | 0.10 | 275 | "279"[a] |

[a]Extrapolation of alarm temperature

We claim as our invention:

1. In combination,
a dynamoelectric machine having parts coated with a material which particulates in response to heat;
means for circulating a stream of cooling fluid in contact with said coated parts;
conduit means connected in fluid communication with said fluid circulating means for extracting a flow of said fluid which has been exposed to said coated parts;
apparatus for sensing the presence of particulate material entrained in said exposed cooling fluid, said apparatus comprising:
a chamber connected in fluid communication with said conduit means for receiving the flow of exposed cooling fluid, said chamber defining a flow path for the exposed cooling fluid;
means for ionizing said exposed cooling fluid disposed within said flow path;
means for collecting ionized particles of said cooling fluid; and,
means for limiting the collection of particle-ion combinations.

2. The combination as defined in claim 1,
said collecting means including first and second electrodes disposed within said flow path of said cooling fluid and downstream with respect to said ionizing means, said electrodes being spaced one from another substantially uniformly by a predetermined distance δ; and,
said limiting means including a source of electrical potential E electrically connected across said electrodes.

3. The combination as defined in claim 2, said cooling fluid being hydrogen gas and the magnitude of the electrical potential E being sufficient to establish a voltage gradient (E/δ) between said electrodes substantially within the range of 1.66 volts per centimeter to 6.66 volts per centimeter.

4. The combination as defined in claim 2 wherein said first and said second electrodes comprise first and second cylindrical conductors, respectively, said first cylindrical electrode being concentrically disposed within said second cylindrical electrode.

5. The combination as defined in claim 4, said first cylindrical electrode having a radius substantially equal to 0.315 centimeters, said second cylindrical electrode having a radius substantially equal to 0.615 centimeters, the magnitude of said electrical potential E being substantially within the range of 0.5 volts to 2.0 volts.

6. The combination as defined in claim 2, said ionized particles of said cooling fluid having an electrical charge of a predetermined electrical polarity, and said first electrode being oppositely charged in polarity with respect to said predetermined polarity of said ionized particles by said source of electrical potential E.

7. Apparatus for sensing the presence of particulate material disposed within a fluid stream comprising:
means for injecting particles emitted by a radioactive material into said stream to effect ionization of said fluid;
means for collecting said ionized particles; and
means for limiting the collection of particle-ion combination.

8. The apparatus defined in claim 7, said means for collecting said ionized particles comprising:
a chamber for receiving said fluid, said chamber having a first port connected in fluid communication with said stream, a second port for discharging said fluid, and portions defining a flow path intermediate of said first and second ports, said radiation particles being injected into said flow path; and,
first and second electrodes disposed in fluid communication with said second port.

9. The apparatus defined in claim 8, said limiting means including a source of electrical potential E electrically connected across said electrodes.

10. The combination as defined in claim 9, said cooling fluid being hydrogen gas and the magnitude of the electrical potential E being sufficient to establish a voltage gradient between said electrodes substantially within the range of 1.66 volts per centimeter to 6.66 volts per centimeter.

* * * * *